(12) United States Patent
Pathi et al.

(10) Patent No.: US 8,003,804 B2
(45) Date of Patent: Aug. 23, 2011

(54) SYNTHESIS OF 4-[1-(4-CYANO PHENYL)-(1,2,4-TRIAZOL-1-YL)METHYL]BENZONITRILE AND 4-[1-(1H-1,2,4-TRIAZOL-1-YL)METHYLENE BENZONITRILE INTERMEDIATE

(75) Inventors: Srinivas Laxminarayan Pathi, Bangalore (IN); Rajendra Narayanrao Kankan, Mumbai (IN); Dharmaraj Ramachandra Rao, Mumbai (IN); Sandip Vasant Chikhalikar, Mumbai (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 12/282,859

(22) PCT Filed: Mar. 19, 2007

(86) PCT No.: PCT/GB2007/000967
§ 371 (c)(1),
(2), (4) Date: Dec. 18, 2008

(87) PCT Pub. No.: WO2007/107733
PCT Pub. Date: Sep. 27, 2007

(65) Prior Publication Data
US 2009/0270633 A1    Oct. 29, 2009

(30) Foreign Application Priority Data

Mar. 17, 2006 (IN) .............................. 376/MUM/2006
Feb. 7, 2007 (IN) .............................. 221/MUM/2007

(51) Int. Cl.
*C07D 249/08* (2006.01)
(52) U.S. Cl. .................................................. 548/262.2
(58) Field of Classification Search ............... 548/262.2; 514/383
See application file for complete search history.

(56) References Cited

U.S. PATENT DOCUMENTS 4,978,672 A * 12/1990 Bowman et al. ............... 514/383
5,391,732 A * 2/1995 Bhatnagar et al. ............ 540/603
7,501,448 B2 * 3/2009 Perlman et al. ............... 514/394
2005/0209294 A1    9/2005 Wadhwa et al.
2007/0066831 A1 * 3/2007 MacDonald et al. ...... 548/262.2

FOREIGN PATENT DOCUMENTS

| EP | 1871750 A1 | 9/2007 |
| WO | 2004076409 A2 | 9/2004 |
| WO | 2004076409 A3 | 9/2004 |
| WO | 2007100346 A1 | 9/2007 |
| WO | 2007107733 A1 | 9/2007 |

OTHER PUBLICATIONS

Yamataka et al. (J. Org. Chem. (1992), 57; p. 2865-2869).*
Andersson et al. (Tetrahedron: Asymmetry, (2004), 15; p. 2539-2545).*
Ahmed et al. (Chem. Comm. (1999), p. 231-232).*
Lin et al. (Tetrahedron (1999), 55; p. 13983-13998).*
Foreign communication from the counterpart application, International Search Report and Written Opinion, Jun. 5, 2007, 10 pages.
Foreign communication from a related counterpart application—Examination Report, GB0817060.7, Jan. 29, 2010, 3 pages.
Foreign communication from the priority application—International Preliminary Report on Patentability, PCT/GB2007/000967, Sep. 23, 2008, 6 pages.

* cited by examiner

*Primary Examiner* — Yong Chu
*Assistant Examiner* — Valerie Rodriguez-Garcia
(74) *Attorney, Agent, or Firm* — Conley Rose, P.C.; Rodney B. Carroll

(57) ABSTRACT

The present invention relates to a process for the preparation of 4-[1-(4-cyano phenyl)-1-(1,2,4-triazol-1-yl)methyl]benzonitrile (letrozole), substantially free from its isomeric impurity. The preparation involves reaction of 4-[1-(1H-1,2,4-triazol-1-yl)methylene benzonitrile with 4-fluorobenzonitrile in the presence of an organic solvent and a silicon amine. The present invention also relates to a process for the preparation of 4-[1-(1H-1,2,4-triazol-1-yl)methylene benzonitrile which involves: (a) the reaction of a 4-halomethyl benzonitrile with 1,2,4-triazole in the presence of cesium carbonate and an organic solvent to obtain a reaction mass comprising 4-[1-(1,2,4-triazole-1-yl)methyl]benzonitrile of formula II; and (b) precipitation of 4-[1-(1,2,4-triazole-1-yl)methyl]benzonitrile (II) from the reaction mass using a suitable organic solvent.

3 Claims, No Drawings

SYNTHESIS OF 4-[1-(4-CYANO PHENYL)-(1,2,4-TRIAZOL-1-YL)METHYL] BENZONITRILE AND 4-[1-(1H-1,2,4-TRIAZOL-1-YL)METHYLENE BENZONITRILE INTERMEDIATE

CROSS-REFERENCE TO RELATED APPLICATIONS

This application is a filing under 35 U.S.C. 371 of International Application No. PCT/GB2007/000967 filed Mar. 19, 2007, entitled "Synthesis of 4-[1-4(4-Cyano Phenyl)-1-(1,2,4-Triazol-1-YL)Methyl]Benzonitrile and 4-[1-(1H-1,2,4-Triazol-1-YL)Methylene Benzonitrile Intermediate," claiming priority of Indian Patent Application Nos. 376/MUM/2006 filed Mar. 17, 2006, and 221/MUM/2007 filed Feb. 7, 2007, which applications are incorporated by reference herein in their entirety.

FIELD OF THE INVENTION

The present invention relates to a process for the preparation of 4-[1-(4-cyano phenyl)-1-(1,2,4-triazol-1-yl)methyl]benzonitrile, a compound of formula I, substantially free of isomeric impurity.

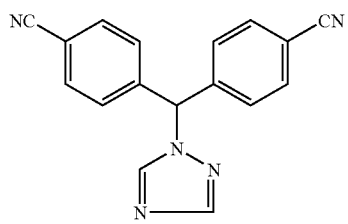

I

The present invention also relates to a process for preparing 4-[1-(1H-1,2,4-triazol-1-yl)methylene benzonitrile, a compound of formula II, an intermediate useful in the preparation of 4-[1-(4-cyano phenyl)-1-(1,2,4-triazol-1-yl)methyl]benzonitrile.

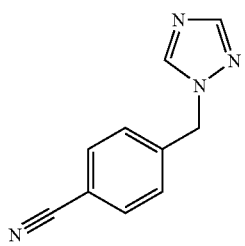

II

BACKGROUND OF THE INVENTION

4-[1-(4-cyano phenyl)-1-(1,2,4-triazol-1-yl)methyl]benzonitrile, or letrozole, is a potent aromatase inhibitor of estrogen biosynthesis which is effective in the treatment of hormone dependent breast cancer in post menopausal women. Estrogen deprivation is most specifically achieved using inhibitors which block the last stage in the biosynthetic sequence, i.e., the conversion of androgens to estrogens by the aromatase enzyme.

Experimental studies demonstrate that letrozole substantially inhibits aromatase activity in both malignant and non-malignant breast tissues, and markedly suppresses endogenous estrogens within the breast cancer.

The last step in the synthesis of letrozole is the reaction of 4-[1-(1H-1,2,4-triazol-1-yl)methylene benzonitrile with 4-fluoro benzonitrile. There are various conditions and reagents disclosed in the prior art for this reaction, including the use of potassium tert-butoxide. All the prior art methods result in letrozole in poor yield. Additionally, the resulting letrozole product requires further purification to eliminate the impurities associated with the reaction to get letrozole with HPLC purity more than 99%.

U.S. Pat. No. 4,978,672 discloses 4-[alpha-(4-cyanophenyl)-1-(1,2,4-triazolyl)-methyl]benzonitrile and a process for its preparation comprising reacting 4-bromomethyl benzonitrile with 1,2,4-triazole to yield 4-[1-(1,2,4-triazol-1-yl)methyl]benzonitrile. 4-[1-(1,2,4-triazol-1-yl)methyl]benzonitrile is then reacted with 4-fluorobenzonitrile to give 4-[1-(4-cyanophenyl)-1-(1,2,4-triazol-1-yl)methyl]benzonitrile (letrozole).

In the process described in '672, the reaction of refluxing 4-bromomethyl benzonitrile with 1,2,4-triazole in the presence of potassium carbonate and potassium iodide in acetone solvent (according to example 24) gives 4-[1-(1,2,4-triazolyl)methyl]benzonitrile of the formula II in an amount of 87 wt %, and 4-[4-(1,2,4-triazol-4-yl)methyl]benzonitrile of the formula III in an amount of 11 wt %, along with 2% of other impurities. The reaction of 4-bromomethyl benzonitrile with 1,2,4-triazole in a mixture of chloroform and acetonitrile (example 9) gives 4-[1-(1,2,4-triazolyl)methyl]benzonitrile of the formula II in an amount of 30 wt %, and 4-[(1,2,4-triazol-4-yl)methyl]benzonitrile of the formula III in an amount of 40 wt %, along with 20 wt % other impurities. The ratios of intended product to impurity for the prior art processes have been determined by experiment.

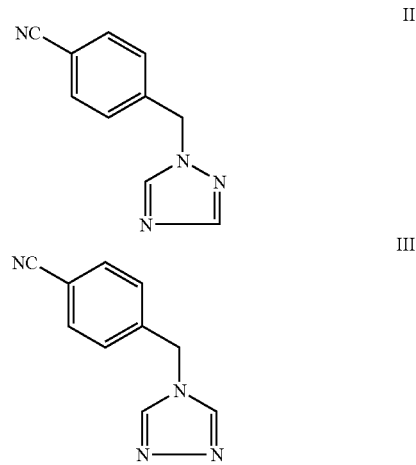

II

III

When the reaction mixture of the above process step is treated with 4-fluorobenzonitrile, it yields 4-[1-(4-cyanophenyl)-1-(1,2,4-triazol-1-yl)-methyl]benzonitrile, a compound of formula I, and its isomer, a compound of formula IV. Thus the impurity of formula III has to be separated before treating it with 4-fluorobenzonitrile, which involves an additional step of column purification which makes the process tedious and extremely disadvantageous in large scale production.

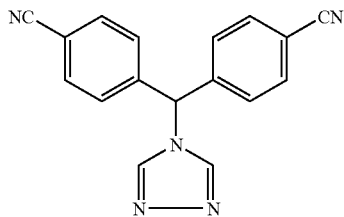

IV

WO 2004/076409 discloses a regiospecific process for preparation of 4-[1-(4-cyano phenyl)-1-(1,2,4-triazol-1-yl) methyl]benzonitrile comprising reacting 4-halomethyl benzonitrile with 4-amino-1,2,4-triazole to give 4-[(4-amino-4H-1,2,4-triazolium-1-yl)methyl]benzonitrile halide, deaminating 4-[(4-amino-4H-1,2,4-triazolium-1-yl)methyl] benzonitrile halide to give 4-[1-(1H-1,2,4-triazol-1-yl)methylene benzonitrile, followed by reacting 4-[1-(1H-1,2,4-triazol-1-yl)methylene benzonitrile with 4-fluorobenzonitrile to obtain letrozole. This application discloses the preparation of letrozole in a 3 step process which involves an additional step of purification of 4-[(4-amino-1,2,4-triazolium-1-yl)methyl] benzonitrile bromide, thereby making the process tedious. The yield of letrozole from 4-bromomethyl benzonitrile is 35% which is low and is not economical. The yield of 4-[(4-amino-4H-1,2,4-triazolium-1-yl)methyl]benzonitrile halide is 98 to 99%, with 1 to 2% unwanted isomeric impurity (compound III).

US 2005/0209294 discloses a process for producing 4-(1H-(1,2,4-triazol-1-yl)methyl)benzonitrile, an intermediate used in the manufacture of letrozole. The application discloses a process using sodium and potassium salts of 1,2, 4-triazole for preparing the compound of formula II. Following the process described in this patent application, 4-(1H-(1, 2,4-triazol-1-yl)methyl)benzonitrile is obtained in a yield of about 60% with 2 to 5% of isomeric impurity (2 to 5% of compound of formula III).

Therefore, the main objective of the present invention is to provide a process for preparation of 4-[1-(4-cyanophenyl)-1-(1,2,4-triazol-1-yl)methyl]benzonitrile of formula I, with a substantially reduced amount of isomeric impurity. Another object of the present invention is to provide simple and economical process for the preparation of 4-[1-(4-cyanophenyl)-1-(1,2,4-triazol-1-yl)methyl]benzonitrile of formula I, resulting in high yields of compound I.

SUMMARY OF THE INVENTION

According to a first aspect of the present invention, there is provided a process for the preparation of 4-[1-(1,2,4-triazole-1-yl)methyl]benzonitrile of formula II,

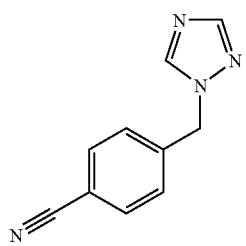

II the process comprising the steps of: (a) reacting a 4-halomethyl benzonitrile with 1,2,4-triazole in the presence of cesium carbonate and an organic solvent to obtain a reaction mass comprising 4-[1-(1,2,4-triazole-1-yl)methyl]benzonitrile of formula II; and (b) precipitating 4-[1-(1,2,4-triazole-1-yl)methyl]benzonitrile (II) from the reaction mass using a suitable organic solvent.

The presence of the cesium carbonate ensures that the possibility of formation of the unwanted impurity (the compound of formula III) is low.

In an embodiment, the organic solvent used in step (a) is selected from the group consisting of alcohols, ketones, nitriles, and other solvents such as dimethylsulphoxide, dimethylformamide, dimethyl acetamide and dichlorobenzene. Preferably, the ketone is acetone.

The 4-halomethyl benzonitrile may be selected from the group consisting of 4-chloromethyl benzonitrile, 4-iodomethyl benzonitrile and 4-bromomethyl benzonitrile.

In an embodiment, the organic solvent used in step (b) is a mixture of two or more organic solvents. Suitably, the organic solvents are non-polar organic solvents. Preferably, the organic solvents used in step (b) are non-polar organic solvents selected from hexane, n-heptane, toluene, xylene, methylene chloride, chlorobenzene, diethyl ether and diisopropyl ether. Most preferably, the solvent mix is a combination of diisopropyl ether and n-heptane.

The reaction can optionally be carried out in the presence of a catalyst, which helps in increasing the rate of the reaction. Preferably, the catalyst is potassium iodide.

The 4-[1-(1,2,4-triazol-1-yl)methyl]benzonitrile produced according to this aspect of the invention may be used to produce 4-[1-(4-cyano phenyl)-1-(1,2,4-triazol-1-yl)methyl] benzonitrile according to known methods, or according to the process of the present invention, as described in the second aspect below.

According to a second aspect of the present invention, there is provided a process for the preparation of 4-[1-(4-cyanophenyl)-1-(1,2,4-triazol-1-yl)methyl]benzonitrile of formula I,

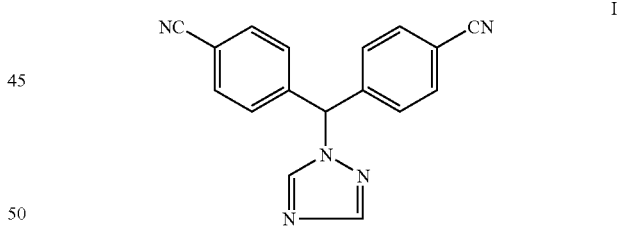

I the process comprising reacting 4-[1-(1H-1,2,4-triazol-1-yl) methylene benzonitrile of formula II

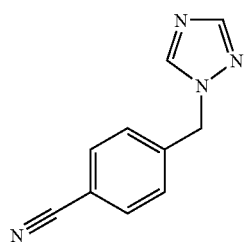

II with 4-fluorobenzonitrile in the presence of an organic solvent and a silicon amine.

The silicon amine may be an alkali metal disilazane or an alkali metal monosilazane. The alkali metal may be selected from lithium, sodium or potassium. Preferably, the silicon amine is an alkali metal disilazane. In an embodiment, the silicon amine is a compound of formula V.

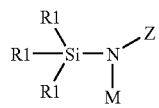

wherein the groups R1 are the same or different and are selected from hydrogen, optionally substituted $C_{1-6}$ alkyl and optionally substituted $C_{2-6}$ alkenyl; Z is selected from hydrogen, $C_{1-6}$ alkyl, $C_{2-6}$ alkenyl and silyl; and M is selected from Li, K, and Na. In an embodiment, the silyl group is $(R2)_3Si—$, wherein R2 has the same meanings as R1. Preferably, R1 is unsubstituted $C_{1-6}$ alkyl. Preferably, R2 is unsubstituted $C_{1-6}$ alkyl. Most preferably, the silicon amine is lithium 1,1,1,3,3,3-hexamethyldisilazane, also termed as Li HMDS.

The use of the silicon amine ensures that the formation of the isomeric impurity (compound IV) is minimised. In particular, the process of the present invention reduces the isomeric impurity (compound IV) to less than 0.1%. A further advantage of the silicon amine is that it is an organic amine, so is soluble in the organic reaction mass. The reactants of the prior art (for example, potassium tertiary butoxide) are not organic and remain as a suspension in the organic reaction mass, slowing down the reaction.

In an embodiment, the organic solvent is selected from 1,4-dioxane, toluene, dichloromethane, dichloroethane and tetrahydrofuran.

The process of the second aspect of the present invention facilitates easy isolation of the product from the reaction mass by simple quenching and filtration. The tedious extraction and recrystallisation process as used in the prior art are thereby avoided.

The reaction of 4-[1-(1H-1,2,4-triazol-1-yl)methylene benzonitrile with 4-fluorobenzonitrile may be carried out at low temperature which further avoids the formation of undesirable by-products. For example, the reaction mass may be cooled to about −30° to −10° C., preferably to a temperature of about −20° C. Typically, the solution of 4-[1-(1H-1,2,4-triazol-1-yl)methyl]benzonitrile in the organic solvent is added to the reaction mass while maintaining temperature below −15° C. Subsequently, the reaction mass may be gradually warmed to about −10° and stirred for about 30 minutes.

The 4-[1-(1,2,4-triazol-1-yl)methyl]benzonitrile starting material may be produced according to known methods, or may be produced according to the process of the present invention, as described in the first aspect above.

According to a third aspect of the present invention, there is provided a process for the preparation of 4-[1-(4-cyanophenyl)-1-(1,2,4-triazol-1-yl)methyl]benzonitrile of formula I, the process comprising: (a) reacting a 4-halomethyl benzonitrile with 1,2,4-triazole in the presence of cesium carbonate and an organic solvent to obtain a reaction mass comprising 4-[1-(1,2,4-triazole-1-yl)methyl]benzonitrile of formula II; (b) precipitating 4-[1-(1,2,4-triazole-1-yl)methyl]benzonitrile (II) from the reaction mass using a suitable organic solvent, and (c) reacting the 4-[1-(1,2,4-triazole-1-yl)methyl] benzonitrile with 4-fluorobenzonitrile in dimethylformamide in the presence of potassium tertiary butoxide.

According to a fourth aspect of the present invention, there is provided a process for the preparation 4-[1-(4-cyanophenyl)-1-(1,2,4-triazol-1-yl)methyl]benzonitrile of formula I, the process comprising: (a) reacting a 4-halomethyl benzonitrile with 1,2,4-triazole in the presence of cesium carbonate and an organic solvent to obtain a reaction mass comprising 4-[1-(1,2,4-triazole-1-yl)methyl]benzonitrile of formula II; (b) precipitating 4-[1-(1,2,4-triazole-1-yl)methyl]benzonitrile (II) from the reaction mass using a suitable organic solvent; and (c) reacting 4-[1-(1,2,4-triazole-1-yl)methyl] benzonitrile with 4-fluorobenzonitrile in the presence of an organic solvent and a silicon amine.

DETAILED DESCRIPTION

In one aspect, the present invention provides an improved process for the production of 4-[1-(1,2,4-triazol-1-yl)methyl] benzonitrile, a compound of formula II. The process results in a product containing an isomeric impurity (i.e. a compound of formula III) of less than 1.0%. The process involves reaction of a 4-halomethyl benzonitrile with 1,2,4-triazole in the presence of cesium carbonate.

According to one embodiment, the process of step (a) is carried out by heating 4-halomethyl benzonitrile with 1,2,4-triazole in the presence of cesium carbonate in an organic solvent. The organic solvent may be an alcohol selected from alkyl alcohols, for example $C_{1-6}$ alkyl alcohols, aryl alcohols, for example $C_{6-12}$ aryl alcohols, or alkylaryl alcohols, for example $C_{7-15}$ alkylaryl alcohols. Suitable alcohols include ethanol, methanol, n-propanol, isopropanol, n-butanol, isobutanol, benzyl alcohol and the like. The organic solvent may be a ketone selected from alkyl ketones, such as $C_{1-6}$ alkyl ketones, aryl ketones, such as $C_{6-12}$ ketones or alkylaryl ketones, such as $C_{7-15}$ ketones. Suitable ketones include acetone, methyl isobutyl ketone and methylethyl ketone. The organic solvent may be a nitrile such as acetonitrile and benzonitrile. Alternatively, the organic solvent may be other solvents selected from dimethylsulphoxide, dimethylformamide, dimethyl acetamide and dichlorobenzene.

The 4-halomethyl benzonitrile may be selected from 4-chloromethyl benzonitrile, 4-iodomethyl benzonitrile and 4-bromomethyl benzonitrile, preferably 4-bromomethyl benzonitrile.

Preferably, step (a) is carried out in a ketonic solvent, more preferably acetone.

Suitably, step (a) is carried out at a temperature ranging from about 20 to 150° C., typically about 40 to 100° C. Preferably, step (a) is carried out a temperature ranging from 40 to 60° C., more preferably 50 to 55° C.

The reaction of step (a) was carried out for about 1 to 5 hours, preferably 2 to 4 hours, more preferably for 3 hours.

The reaction of step (a) can be optionally carried out in the presence of a catalyst, preferably potassium iodide.

In the process of step (b), the organic layer containing compound II may be washed with acidified saturated sodium chloride solution, the insolubles infiltered and then the solution concentrated under vacuum to give a residue. The residue may then be precipitated by adding a mixture of two or more solvents. Preferably, the organic solvents are non-polar organic solvents. The solvents may be selected from: halo-substituted or unsubstituted alkyl hydrocarbons; and halo-substituted, unsubstituted or alkyl-substituted aryl hydrocarbons. Suitably, the organic solvents may be hexane, n-heptane, toluene, xylene, methylene chloride, chlorobenzene, and ethers like diethyl ether and diisopropyl ether. Preferably a mixture of diisopropyl ether and n-heptane is used. The solution containing the solids may then be cooled to below 25° C., preferably 10° C., stirred, filtered and washed with an aprotic solvent selected from aliphatic hydrocarbon, aromatic hydrocarbons and the like, most preferably n-heptane to yield compound II with less than 1.0% isomeric impurity (compound III).

In an embodiment, the process further comprises reacting the 4-[1-(1,2,4-triazole-1-yl)methyl]benzonitrile of formula II with 4-fluorobenzonitrile to yield 4-[1-(4-cyanophenyl)-1-(1,2,4-triazol-1-yl)methyl]benzonitrile of formula I. This further step may be carried out by treating the compound of formula II with 4-fluorobenzonitrile in an organic solvent such as dimethylformamide in the presence of a base such as potassium tertiary butoxide. The reaction may be carried out at a temperature ranging from 5 to 10° C. The 4-[1-(4-cyanophenyl)-1-(1,2,4-triazol-1-yl)methyl]benzonitrile of formula I will contain substantially less of isomeric impurity (compound IV), which arises due to a side reaction of compound III (the isomeric impurity from the previous step) with 4-fluorobenzonitrile.

The reaction mixture may be worked up by extracting with an organic solvent, concentrating and optionally purifying to yield 4-[1-(4-cyanophenyl)-1-(1,2,4-triazol-1-yl)methyl]benzonitrile, a compound of formula I, containing less than 0.1% of the isomeric impurity. Compound I may be recrystallised with a solvent selected from polar and non-polar solvents such as alcohols, ketones and esters, preferably methanol.

The further step of reacting the 4-[1-(1,2,4-triazole-1-yl)methyl]benzonitrile of formula II with 4-fluorobenzonitrile to yield 4-[1-(4-cyanophenyl)-1-(1,2,4-triazol-1-yl)methyl]benzonitrile of formula I, may be carried out in the presence of an organic solvent and a silicon amine. This is the same step as is described below in the second aspect of the present invention. The 4-[1-(1,2,4-triazole-1-yl)methyl]benzonitrile of formula II from the first step may be isolated with or without drying before reaction with 4-fluorobenzonitrile.

4-[1-(4-cyanophenyl)-1-(1,2,4-triazol-1-yl)methyl]benzonitrile I, provided by these embodiments has purity greater than 99.0%, with isomeric impurity (compound IV) less than 0.1%.

According to a second aspect of the present invention, there is provided a process for the preparation of 4-[1-(4-cyanophenyl)-1-(1,2,4-triazol-1-yl)methyl]benzonitrile of formula I, the process comprising reacting 4-[1-(1H-1,2,4-triazol-1-yl)methylene benzonitrile of formula II with 4-fluorobenzonitrile in the presence of an organic solvent and a silicon amine.

The silicon amine may be an alkali metal disilazane or an alkali metal monosilazane. The alkali metal may be selected from lithium, sodium or potassium. Preferably, the silicon amine is an alkali metal disilazane. In an embodiment, the silicon amine is a compound of formula V.

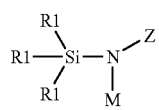

wherein the groups R1 are the same or different and are selected from hydrogen, optionally substituted $C_{1-6}$ alkyl and optionally substituted $C_{2-6}$ alkenyl; Z is selected from hydrogen, $C_{1-6}$ alkyl, $C_{2-6}$ alkenyl and silyl; and M is selected from Li, K, and Na. In an embodiment, the silyl group is $(R2)_3Si-$, wherein R2 has the same meanings as R1. Preferably, R1 is unsubstituted $C_{1-6}$ alkyl. Preferably, R2 is unsubstituted $C_{1-6}$ alkyl.

The process of the present invention employs very mild conditions and it avoids the formation of impurities. Li-HMDS is the preferred silicon amine. Tetrahydrofuran is the preferred organic solvent. The reaction mass is cooled to about −30° to −10° C. Suitably, the reaction mass is cooled to a temperature ranging of −30° to −15° C., preferably to a temperature of about −20° C. Further a solution of 4-[1-(1H-1,2,4-triazol-1-yl)methyl]benzonitrile in an organic solvent selected from 1,4-dioxane, toluene, dichloromethane, dichloroethane, preferably tetrahydrofuran is added to the above reaction mass maintaining temperature below −15° C. The reaction mass is gradually warmed to about −10° and stirred for 30 minutes. After completion of reaction, the reaction mass is quenched in water below 10° C. The reaction mass is stirred for 2-3 hrs between 10-20° C., and the resulting solid is filtered and dried under vacuum to get letrozole with high purity.

The preferred embodiment is schematically represented below.

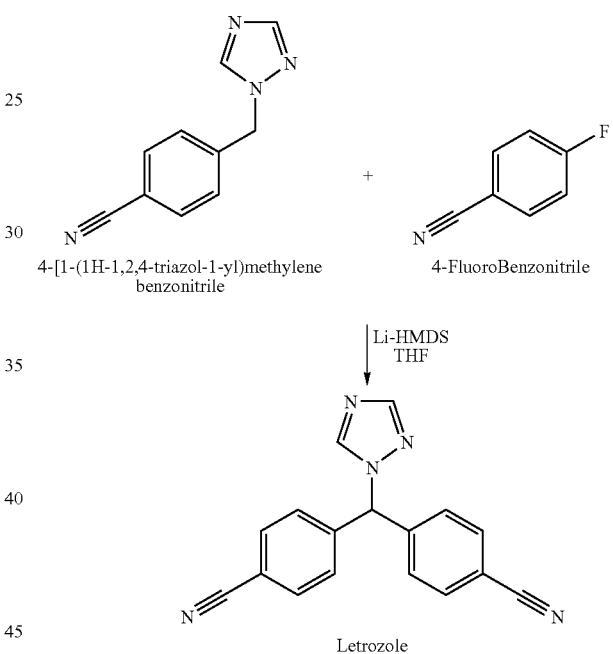

The process of this invention has addressed the problems of the prior art and has also provided technological advancement as well as economic benefit through cost reduction and elimination of avoidable steps of additional purification steps involving complex column chromatography.

The details of the invention are given in the following examples, which are provided for illustration only and should not be construed to limit the scope of the invention.

EXAMPLES

Example 1

Preparation of 4-[1-(1,2,4-triazole-1-yl)methyl]benzonitrile, Compound of Formula II Acetone (1500 ml), 1,2,4-triazole (200 gm; 2.895 mol. eq), cesium carbonate (142 gm; 0.436 mol. eq) and potassium iodide (9 gm) was heated to reflux (55° C.) for 4 hours. The reaction mixture was cooled to room temperature. To this, a solution of 4-bromomethyl benzonitrile (100 gm; 0.510 mol. eq) in dichloromethane (450 ml) was added over a period of 2 hours. The reaction mixture was refluxed for 3 hours. After the completion of reaction, the mass was cooled to 25° C. and the insolubles filtered. The filtrate was concentrated to residue under vacuum. The residue was dissolved in dichloromethane (500 ml), washed with saturated solution of sodium chloride, acidified to a pH 1.0 with concentrated hydrochloric acid and concentrated under vacuum. To the residue, a mixture of diisopropyl ether (160 ml) and n-Heptane (160 ml) was added, stirred at 10° C. for 30 minutes, filtered, washed with n-Heptane and dried under vacuum at 40-45° C. to give 4-[1-(1,2,4-triazole-1-yl)methyl]benzonitrile (76 gm, 81% yield, 99.0% HPLC purity).

Example 2

Preparation of 4-[1-(4-cyanophenyl)-1-(1,2,4-triazol-1-yl)methyl]benzonitrile, Compound of Formula I A solution of 4-[1-(1,2,4-triazolyl)methyl]benzonitrile (100 gm; 0.543 mol. eq) in dimethyl formamide (480 ml) was added at a temperature of −5 to 0° C. under nitrogen atmosphere to a solution of potassium tertiary butoxide (192 gm; 1.711 mol. eq) in dimethyl formamide (800 ml) over a period of 90 minutes and further stirred for 30 minutes.

To this solution, a solution of 4-fluorobenzonitrile (92 gm; 0.760 mol. eq) in dimethyl formamide (480 ml) was added at temperature of 0-5° C. and stirred at 5-10° C. for 15 minutes. After the completion of reaction, water was added at 5-10° C. and the product was extracted with ethyl acetate. The organic layer was washed with water and concentrated under vacuum below 40° C. to give a syrupy liquid, to which n-Heptane (160 ml) was added, stirred at 25-30° C. for 15 minutes, filtered and washed with n-Heptane to give the crude product.

The crude product was dissolved in methanol (15 volumes) at reflux temperature, treated with activated charcoal (20 gm), filtered at hot and the filtrate was concentrated to a minimum volume. The contents were then cooled to 0-5° C. for 30 minutes, filtered, washed with methanol. The product so filtered was slurried in methanol-acetone mixture at 40-45° C. for 30 minutes, cooled to 20-25° C., filtered, washed with methanol and dried under vacuum at 40-45° C. to give 4-[1-(4-cyanophenyl)-1-(1,2,4-triazol-1-yl)methyl]benzonitrile (113-120 gm, 73-77.5% yield, >99.7% HPLC purity).

Example 3

Preparation of 4-[1-(4-cyanophenyl)-1-(1,2,4-triazol-1-yl)methyl]benzonitrile, Compound of Formula I Li-HMDS in tetrahydrofuran solution (0.79 lit, 1.41 mol) was taken in a clean and dry flask. It was then cooled to −20° C. and a solution of 4-fluorobenzonitrile (60 gm, 0.495 mol) in tetrahydrofuran (100 ml) was added below −20° C. The reaction mass was stirred for 5 min and a solution of 4-[1-(1,2,4-triazolyl)methyl]benzonitrile (100 gm, 0.5434 mol.) in 300 ml tetrahydrofuran was added slowly below −15° C. The reaction mass was stirred at same temperature for 30 min. and quenched with water (5 lit.) below 10° C. The reaction mass was stirred for 2-3 hours between 10-20° C., the solid was filtered and washed with water (1 lit.) to get 130 gms of 4-[1-(4-cyano phenyl)-1-(1,2,4-triazol-1-yl)methyl]benzonitrile having HPLC purity 99.5%.

Example 4

Preparation of 4-[1-(4-cyano phenyl)-1-(1,2,4-triazol-1-yl)methyl]benzonitrile, Compound of Formula I 4-[1-(1,2,4-triazolyl)methyl]benzonitrile (50 gm., 0.2717 mol) and (30 gm, 0.2479 mol) 4-fluorobenzonitrile was introduced into the reactor under dry atmosphere along with tetrahydrofuran (0.5 lit). The reaction mass was cooled to −20° C. and a tetrahydrofuran solution of Li-HMDS (0.38 lit, 0.6826 mol) was added to the reaction mass in 1 hour at a temperature below −15° C. The reaction mass was stirred for 1 hour at −10° C. to −5° C. and quenched with saturated sodium chloride solution (3 lit.) at a temperature below 10° C. The reaction mass was further stirred for 2-3 hrs at a temperature between 10-20° C. The resulting solid was filtered and washed with water to get 50 gms of 4-[1-(4-cyanophenyl)-1-(1,2,4-triazol-1-yl)methyl]benzonitrile.

Example 5

Preparation of 4-[1-(4-cyanophenyl)-1-(1,2,4-triazol-1-yl)methyl]benzonitrile Compound of Formula I 4-[1-(1,2,4-triazolyl)methyl]benzonitrile (150 gm, 0.81 mol) was dissolved in tetrahydrofuran (750 ml) at room temperature under inert atmosphere. This mixture was then cooled to −30° C. and Li-HMDS in tetrahydrofuran solution (1.14 lit, 2.0 mol) was added drop wise in 30 minutes at a temperature below −25° C. The reaction mass was stirred at −25° C. for 10 minutes and a solution of 4-fluorobenzonitrile (90 gm, 0.7438 mol) in tetrahydrofuran (0.25 lit) was added slowly in about 30 minutes maintaining the temperature below −20° C. The reaction mass was stirred at −20° C. to −15° C. for 45 minutes and quenched with water (7.5 lit.) at a temperature below 10° C. The quenched reaction mass was extracted four times with ethyl acetate (2.5 lit.). Combined organic layers were washed twice with brine (1 lit). Dried ethyl acetate layer over sodium sulfate and concentrated to obtain product. The obtained product was refluxed with Isopropanol (900 ml) for 1 hour at 80° C., cooled gradually to 25-30° C. and filtered to get 150 gm of 4-[1-(4-cyano phenyl)-1-(1,2,4-triazol-1-yl)methyl]benzonitrile.

Example 6

Preparation of 4-[1-(4-cyanophenyl)-1-(1,2,4-triazol-1-yl)methyl]benzonitrile, Compound of Formula I a) Acetone (2000 ml), 1,2,4-triazole (260 gm; 3.826 mol. eq), cesium carbonate (188 gm; 0.577 mol. eq) and potassium iodide (12 gm) was heated to reflux (55° C.) for 4 hours. The reaction mixture was cooled to room temperature. To this, a solution of 4-bromomethyl benzonitrile (132 gm; 0.673 mol. eq) in dichloromethane (600 ml) was added over a period of 2 hours. The reaction mixture was refluxed for 3 hours. After the completion of reaction, the mass was cooled to 25° C. and the insolubles filtered. The filtrate was concentrated to residue under vacuum. The residue was dissolved in dichloromethane (750 ml), washed with saturated solution of sodium chloride, acidified to a pH 1.0 with concentrated hydrochloric acid and concentrated under vacuum. To the residue, a mixture of diisopropyl ether (210 ml) and n-Heptane (210 ml) was added, stirred at 10° C. for 30 minutes, the resulting solid was filtered, washed with n-Heptane and taken for next step.

b) Li-HMDS in tetrahydrofuran solution (0.79 lit, 1.41 mol) was taken in a clean and dry flask. It was then cooled to −20° C. and a solution of 4-fluorobenzonitrile (60 gm, 0.495 mol) in tetrahydrofuran (100 ml) was added below −20° C. The reaction mass was stirred for 5 minutes and a solution of 4-[1-(1,2,4-triazolyl)methyl]benzonitrile (100 gm, 0.5434 mol. (obtained from step above (a)) in 300 ml tetrahydrofuran was added slowly below −15° C. The reaction mass was stirred at same temperature for 30 minutes and quenched with water (5 lit.) below 10° C. The reaction mass was stirred for 2-3 hours between 10-20° C., the solid was filtered and washed with water (1 lit.) to get 130 gms of 4-[1-(4-cyano phenyl)-1-(1,2,4-triazol-1-yl)methyl]benzonitrile having HPLC purity 99.5%.

It will be appreciated that the invention may be modified within the scope of the appended claims.

The invention claimed is:

1. A process for the preparation of 4-[1-(4-cyanophenyl)-1-(1,2,4-triazol-1-yl)methyl]benzonitrile of formula I,

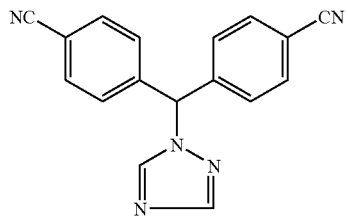

I the process comprising reacting 4-[1-(1H-1,2,4-triazol-1-yl)methylene benzonitrile of formula II

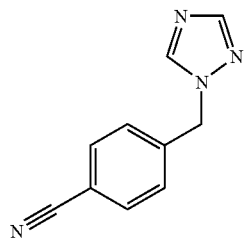

II with 4-fluorobenzonitrile in the presence of an organic solvent and a silicon amine, wherein the silicon amine is lithium 1,1,1,3,3,3-hexamethyldisilazane and, wherein the lithium 1,1,1,3,3,3-hexamethyldisilazane is first contacted with 4-fluorobenzonitrile to form a first mixture and the first mixture is subsequently contacted with the 4-[1-(1H-1,2,4-triazol-1-yl)methylene benzonitrile of formula II.

2. The process according to claim 1, wherein the organic solvent is selected from 1,4-dioxane, toluene, dichloromethane, dichloroethane and tetrahydrofuran.

3. The process according to claim 1, wherein the 4-[1-(1,2,4-triazole-1-yl)methyl]benzonitrile of formula II is prepared by a process comprising the steps of: (a) reacting a 4-halomethyl benzonitrile with 1,2,4-triazole in the presence of cesium carbonate and an organic solvent to obtain a reaction mass comprising 4-[1-(1,2,4-triazole-1-yl)methyl]benzonitrile of formula II; and (b) precipitating 4-[1-(1,2,4-triazole-1-yl)methyl]benzonitrile (II) from the reaction mass using a suitable organic solvent.

* * * * *